United States Patent [19]

Walker

[11] 4,277,634

[45] Jul. 7, 1981

[54] PROCESS FOR THE SELECTIVE HOMOLOGATION OF METHANOL TO ETHANOL

[75] Inventor: Wellington E. Walker, Sissonville, W. Va.

[73] Assignee: Union Carbide Corporation, New York, N.Y.

[21] Appl. No.: 138,688

[22] Filed: Apr. 9, 1980

[51] Int. Cl.$^3$ .................. C07C 27/00; C07C 29/36
[52] U.S. Cl. ............................................. 568/902
[58] Field of Search ......................................... 568/902

[56] References Cited

U.S. PATENT DOCUMENTS

| | | | |
|---|---|---|---|
| 3,248,432 | 4/1966 | Riley et al. ............................. | 568/902 |
| 3,285,948 | 11/1966 | Butter ..................................... | 568/902 |
| 4,133,966 | 1/1979 | Pretzer et al. ......................... | 568/902 |
| 4,168,391 | 9/1979 | Slinkard ................................ | 568/902 |
| 4,205,190 | 5/1980 | Gane et al. ............................ | 568/902 |

FOREIGN PATENT DOCUMENTS

| | | | |
|---|---|---|---|
| 1937 | 5/1979 | European Pat. Off. ................ | 568/902 |
| 3876 | 9/1979 | European Pat. Off. ................ | 568/902 |

*Primary Examiner*—Joseph E. Evans
*Attorney, Agent, or Firm*—Francis M. Fazio

[57] ABSTRACT

A process for the production of ethanol from the cobalt-catalyzed, iodide-promoted reaction of methanol, hydrogen and carbon monoxide, attaining selectivity to ethanol heretofore unachievable at high methanol conversion, wherein the reaction is carried out in an inert solvent, at a temperature of from greater than 180° C. to 220° C. with an iodide to cobalt mole ratio of from 0.1:1 to 4:1.

11 Claims, No Drawings

PROCESS FOR THE SELECTIVE HOMOLOGATION OF METHANOL TO ETHANOL

BACKGROUND OF THE INVENTION

As the price of petroleum continues to increase and as the availability of petroleum becomes more questionable, ethanol is becoming increasingly more important as a source of hydrocarbon-based fuels and chemicals. Ethanol has long been produced by the well known fermentation process. Another more recent process of producing ethanol is by the reaction of methanol with hydrogen and carbon monoxide (syn gas). This method has significant advantages because relatively inexpensive reactants are employed.

It has long been known that a water soluble cobalt catalyst will catalyze the reaction of methanol, hydrogen and carbon monoxide to produce ethanol. This cobalt-catalyzed reaction gives acceptable selectivity to ethanol, approximately 70 percent, but is plagued by poor methanol conversion of only about 50 percent. Practitioners of the art have attempted to increase the methanol conversion of this reaction by adding to the cobalt catalyst an iodide promoter; this has succeeded in increasing methanol conversion to over 90 percent but this increased activity results in a deleterious effect on ethanol selectivity, reducing it to about 25 percent and thereby severely limiting the ethanol yield. To overcome these problems, those skilled in the art have altered this catalyst system by the introduction of phosphorus compounds (U.S. Pat. No. 3,248,432) or by the addition of osmium or ruthenium halide promoters (U.S. Pat. No. 3,285,948). Unfortunately these catalyst systems are generally costly and cumbersome and in some cases relatively unstable, due to their complexity. It is interesting to note that both of these patents, U.S. Pat. No. 3,248,432 at column 1 lines 25–37 and U.S. Pat. No. 3,285,948 at column 1; lines 35–47 emphasize the poor selectivity to ethanol when the reaction is catalyzed by a system containing only cobalt and iodine. A process which can utilize the relatively simple cobalt-iodide catalyst system to produce ethanol from the reaction of methanol, hydrogen and carbon monoxide at high ethanol selectivity and at high methanol conversion would be of great advantage.

SUMMARY OF THE INVENTION

It has now been found that ethanol can be produced from the cobalt-catalyzed iodide-promoted homologation reaction of methanol, hydrogen and carbon monoxide at an ethanol selectivity and a methanol conversion heretofore simultaneously unachievable by carrying out the reaction at from greater than 180° C. to 220° C., in the presence of certain inert solvents, when the iodide to cobalt mole ratio is from 0.1:1 to 4:1.

DESCRIPTION OF THE INVENTION

This invention is an improved catalytic method for selectively producing ethanol from methanol, hydrogen and carbon monoxide. Furthermore, any compounds which will form hydrogen and carbon monoxide, such as the mixture of water and carbon monoxide or the mixture of hydrogen and carbon dioxide, can be used as a substitute for the mixture of hydrogen and carbon monoxide used herein to exemplify the present invention.

In the process of this invention the reaction is run in a substantially inert solvent; the presence of the inert solvent being critical to the attainment of high ethanol selectivity at high methanol conversion. Any inert solvent which does not inhibit the homologation reaction can be used in the improved process of this invention and illustrative thereof one can name dioxane, toluene, tetrahydrofuran, the dimethyl ether of tetraethylene glycol, 1,2-dimethoxybenzene and the like. The preferred inert solvent is dioxane. The inert solvent is present in a volume ratio of solvent to methanol of from about 0.5:1 to about 100:1, preferably from about 1:1 to about 10:1, most preferably from about 1:1 to about 3:1.

The temperature at which the reaction is carried out is critical for the selective production of ethanol and can vary from greater than 180° C. to 220° C., preferably from 190° C. to 210° C..

The pressure of the reaction can vary from 1000 psig to 10,000 psig or higher, preferably from 1500 psig to 5000 psig.

The mole ratio of hydrogen to carbon monoxide is from 1:10 to 10:1; preferred being from about 1:1 to about 4:1.

The catalyst system for the improved homologation process of this invention contains a cobalt catalyst and an iodine or iodide promoter. The cobalt-iodide catalyst system is present in a catalytically effective amount, sufficent to catalyze the reaction, preferably from 0.5 to 25 weight percent, most preferably from 1 to 10 weight percent, based on the amount of methanol present.

The cobalt component of the catalyst system can be furnished from a number of sources, for example, any of known cobalt carboxylates such as cobalt formate, cobalt acetate, cobalt propionate, cobalt butyrate, cobalt valerate, cobalt hexanonate, and the like; the known cobalt carbonyl compounds such as dicobalt octacarbonyl, methyl cobalt tetracarbonyl, acetyl cobalt tetracarbonyl, and the like, or their phosphine substituted analogs many of which are known to those skilled in the art; cobalt oxide and cobalt hydroxide, cobalt carbonate and cobalt bicarbonate; and the soluble cobalt halides such as cobalt iodide, cobalt bromide and cobalt chloride. A convenient source of cobalt is cobalt acetate.

The mole ratio of cobalt to methanol can be from 1:5 to 1:20,000, preferably from 1:50 to 1:500.

The iodide promoter of the catalyst system can come from any iodine-containing source which is capable of ionizing so as to supply iodide ion to the reaction. Illustrative as sources of the iodide atom are elemental iodine, cobalt iodide, potassium iodide, lithium iodide, hydrogen iodide, the alkyl iodides having from 1 to 10 carbon atoms such as methyl iodide, propyl iodide, 2-ethylhexyl iodide, n-decyl iodide, and the like, the organic ammonium iodides of the formula $R_4NI$ and the organic phosphonium iodides of the formula $R_4PI$ wherein R is alkyl having from 1 to 10 carbon atoms or aryl having from 6 to 10 ring carbon atoms such as tetramethyl ammonium iodide, tetraethyl ammonium iodide, tetraethylhexyl ammonium iodide, tetraphenyl ammonium iodide, tetramethyl phosphonium iodide, tetrapropyl phosphonium iodide, tetraethylhexyl phosphonium iodide, tetraphenyl phosphonium iodide, and the like. The preferred source of the iodide is elemental iodine.

The mole ratio of iodide to cobalt in the catalyst mixture is critical for the selective production of ethanol at high methanol conversion by use of the improved process of this invention. The mole ratio of iodide to cobalt is from 0.1:1 to 4:1 and preferably it is from about 0.5:1 to 2:1.

The reaction time will vary and is dependent on batch size, other reaction parameters employed and the specific components used in the cobalt-iodide catalyst system.

In a typical embodiment of a laboratory scale batch process, methanol is charged to a reactor with the inert solvent and a catalyst system containing a cobalt compound and an iodide compound; the reactor is purged, charged with the hydrogen/carbon monoxide gas mixture, sealed heated until the desired reaction is completed. It is well known that commercially this process could be run continuously.

The improved process of this invention allows for the selective production of ethanol from the cobalt-catalyzed, iodide-promoted homologation reaction of methanol, hydrogen and carbon monoxide, at a methanol conversion and ethanol selectivity heretofore simultaneously unachievable by the processes known to those skilled in the art. By use of the improved process of this invention ethanol can be produced significantly more economically that was heretofore possible. This highly advantageous result was unexpected and could not have been predicted.

The following examples serve to further illustrate the improved process of this invention. In these examples and in the experiments which also follow, methanol conversion is calculated as (grams MeOH charged-grams MeOH discharged)/(grams MeOH charged)×100 and selectively is calculated as (grams EtOH/grams total proeduct)×100 and the following abbreviations are used:

MeOH—methanol
EtOH—ethanol
AcH—acetaldehyde
PrOH—propanol
PrH—propionaldehyde
MeOAc—methyl acetate
EtOAc—ethyl acetate
DMAc—dimethyl acetal

EXAMPLE 1

In this series of runs, a 316 stainless steel lined 250 cc autoclave was charged with 20 ml of reagent grade methanol and 60 cc of dioxane along with cobalt acetate and elemental iodine in the amounts indicated in Table I. The reactor was sealed, purged with carbon monoxide and then pressurized to 3000 psig with a gaseous mixture having a 2:1 molar ratio of hydrogen and carbon monoxide. The reactor and its contents were heated at 190° C. for the indicated time during which the reactor contents were stirred to obtain thorough mixing. During the reaction the average pressure in the reactor was about 3500 psig. After this period the reactor was cooled to 25°–30° C. and vented, and the liquid reaction product mixture was recovered and analyzed using a vapor phase gas chromatograph equipped with a thermal conductivity detector and a ⅛ inch by 6 foot column packed with a commercially available polystyrene resin commonly used for gas chromatography. The results are reported in Table I.

For comparative purposes two control runs were carried out using the above described procedure except that in Control Run A there was no iodine employed and in Control Run B the amount of iodine employed exceeded the amount found critical. The results of these control runs are also reported in Table I.

TABLE I

| Run | Co. (mmoles) | $I_2$ (mmoles) | Mole Ratio I/Co | Time (hrs) | MeOH Conversion % | Selectivity (%) | | | |
|---|---|---|---|---|---|---|---|---|---|
| | | | | | | EtOH | AcH | MeOAc | EtOAc |
| 1 | 12 | 12 | 2:1 | 3 | 92 | 61.4 | 9.4 | 19.5 | 9.7 |
| 2 | 6 | 3 | 1:1 | 4 | 93 | 69.5 | 5.6 | 19.8 | 5.1 |
| 3 | 12 | 6 | 1:1 | 4 | ~100 | 65.5 | 1.7 | 23.2 | 9.6 |
| 4 | 12 | 3 | 0.5:1 | 4 | 90 | 68.4 | 2.6 | 22.3 | 6.7 |
| Control A | 12 | 0 | 0 | 4 | 50.6 | 69.2 | 1.9 | 24.3 | 4.6 |
| Control B | 3 | 12 | 8:1 | 3 | 97.5 | 23.3 | 49.3 | 8.2 | 19.2 |

The results achieved in Runs 1 to 4 demonstrate that the improved process of this invention effectively produces ethanol from methanol, hydrogen and carbon monoxide at both high methanol conversion and high ethanol selectivity. This is readily apparent when the results of Runs 1 to 4 are compared to the Control runs. Thus, while Control A, in which the I:Co mole ratio was below that which was found critical, showed an acceptable selectivity to ethanol, the methanol conversion was low; in Control B, in which the I:Co mole ratio was above that which was found critical, though the methanol conversion was high, the selectivity to ethanol was not acceptable. The results of Controls A and B show that when the reaction conditions are outside the limits defined in this invention one does not obtain both high methanol conversion and high ethanol selectivity; on the other hand in Runs 1 to 4 one does obtain both.

EXAMPLE 2

A series of runs was carried out, each run using a procedure similar to that described in Example 1 but with the variations indicated in Table II. The I:Co ratio in each run was 0.5:1 using 12 mmoles of cobalt acetate and 3 mmoles of elemental iodine. The reaction products were analyzed as in Example 1 and the results, reported in Table II, further demonstrate the high methanol selectivity at high methanol conversion of the improved process of this invention.

TABLE II

| Run | Time (hrs) | Temp. (°C.) | Initial Pressure (psig) | Average Reaction Pressure (psig) | Mole Ratio ($H_2$/CO) | MeOH Conversion % | Selectivity (%) | | | |
|---|---|---|---|---|---|---|---|---|---|---|
| | | | | | | | EtOH | AcH | PrOH PrH MeOAc | EtOAc |
| 1 | 2 | 210 | 3000 | 3500 | 2:1 | 77 | 65.2 | 9.7 | 19.3 | 5.8 |
| 2 | 4 | 210 | 3000 | 3500 | 2:1 | 91 | 63 | 12.4 | 17.9 | 6.7 |
| 3 | 3 | 190 | 5000 | 6000 | 3:2 | 83 | 68.2 | 2.4 | 23.5 | 5.9 |
| 4 | 4 | 190 | 5000 | 6000 | 4:1 | 80 | 70 | 1.6 | 23.7 | 4.7 |

TABLE II-continued

| Run | Time (hrs) | Temp. (°C.) | Initial Pressure (psig) | Average Reaction Pressure (psig) | Mole Ratio ($H_2/CO$) | MeOH Conversion % | Selectivity (%) | | | |
|---|---|---|---|---|---|---|---|---|---|---|
| | | | | | | | EtOH | AcH | PrOH PrH MeOAc | EtOAc |
| 5 | 3 | 190 | 5000 | 6000 | 1:1 | 90 | 67.9 | 2.1 | 22.4 | 7.6 |
| 6 | 5 | 190 | 1500 | 1750 | 2:1 | 70 | 75.3 | 2.9 | 16.5 | 5.3 |

COMPARATIVE EXPERIMENT A

A series of runs was carried out using a procedure similar to that described in Example 1 except that one or more of the parameters of solvent, temperature, and I:Co ratio, found critical in the improved process of this invention, was not employed. In each run the cobalt source was cobalt acetate and the iodide source was elemental iodine, except in Run 1 when iodide was not employed. The other reaction conditions are shown in Table III. The reaction products of each run were analyzed as in Example 1 and the analytical results are reported in Table IV.

aldehydes, esters and alcohols containing more than 4 carbon atoms.

In Run 1, the iodine promoter and inert solvent were absent; methanol conversion and selectivity to ethanol were only about 50 percent.

While Run 2 was carried out with an I:Co mole ratio and temperature within the ranges recited by applicant there was no inert solvent; the consequence was low ethanol selectivity even though methanol conversion was high. This demonstrates that the presence of the inert solvent is critical to the attainment of high ethanol selectivity at high methanol conversion.

In Runs 3 to 5 the temperature was outside the range

TABLE III

| Run | Co (mmoles) | $I_2$ (mmoles) | Mole Ratio I/Co | MeOH (ml) | Dioxane (ml) | Time (hrs) | Temp. (°C.) | Initial Pressure (psig) | Average Reaction Pressure (psig) | Mole Ratio $H_2/CO$ |
|---|---|---|---|---|---|---|---|---|---|---|
| 1 | 6 | 0 | 0 | 60 | 0 | 5 | 190 | 3000 | 3500 | 2:1 |
| 2 | 6 | 3 | 1:1 | 60 | 0 | 5 | 190 | 2000 | 2400 | 1:1 |
| 3 | 6 | 12 | 4:1 | 60 | 0 | 5 | 160 | 2000 | 2400 | 1:1 |
| 4 | 6 | 12 | 4:1 | 60 | 0 | 2 | 160 | 3000 | 3500 | 1:1 |
| 5 | 6 | 12 | 4:1 | 60 | 0 | 5 | 140 | 3000 | 3500 | 2:1 |
| 6 | 6 | 12 | 4:1 | 20 | 60 | 2 | 160 | 3000 | 3500 | 2:1 |
| 7 | 6 | 12 | 4:1 | 20 | 60 | 5 | 140 | 3000 | 3500 | 2:1 |
| 8 | 6 | 12 | 4:1 | 20 | 60 | 5 | 120 | 3000 | 3500 | 2:1 |
| 9 | 3 | 12 | 8:1 | 20 | 60 | 3 | 160 | 3000 | 3500 | 2:1 |
| 10 | 3 | 12 | 8:1 | 20 | 60 | 5 | 140 | 3000 | 3500 | 2:1 |

TABLE IV

| Run | Methanol Conversion % | Product Distribution (wt %) | | | | | | | | |
|---|---|---|---|---|---|---|---|---|---|---|
| | | EtOH | AcH | AcOH | PrOH PrH and/or MeOAc | | EtOAc and/or DMAc | | HEAVIES | |
| 1 | 46 | 59.1 | — | — | 19.1 | (a) | 12.2 | (d) | 9.6 | |
| 2 | 89 | 21.7 | 4.1 | 20.8 | 16 | (b) | 19.1 | (e) | 18.3 | |
| 3 | 89 | 1 | 17.8 | 26.1 | 30.8 | (b) | 13 | (e) | 11.3 | |
| 4 | 74 | 1.2 | 34.6 | 1.3 | 33.4 | (b) | 20.6 | (e) | 7.2 | |
| 5 | 70 | 0.8 | 32.6 | — | 32 | (b) | 25.1 | (e) | 9.4 | |
| 6 | 82 | 2.9 | 72 | — | 11.6 | (b) | 13.5 | (f) | — | |
| 7 | 93 | 3.3 | 74.5 | — | 7.7 | (c) | 14.5 | (f) | — | |
| 8 | 77 | — | 68.5 | — | 10.5 | (b) | 21 | (f) | — | |
| 9 | 84 | 2.8 | 73.4 | — | 7.7 | (b) | 16.1 | (f) | — | |
| 10 | 88 | 3.8 | 75.8 | — | 6.3 | (c) | 14.1 | (f) | — | |

(a) Mixture of PrOH and MeOAc
(b) MeOAc only
(c) Mixture of PrH and MeOAc
(d) EtOAc only
(e) Mixture of EtOAc and DMAc
(f) DMAc only The results of this experiment demonstrate the generally overall poor results obtained when the process of this invention is not employed. The basic concept of this invention is the discovery that the three parameters must be controlled within the critical limits recited and act in concert. The results of this comparative experiment clearly demonostrate this.

The products listed as HEAVIES in the table were higher molecular weight oxygenated products such as recited by applicant and in addition inert solvent was absent; in all instances the ethanol selectivity was low even though methanol conversion was high.

Runs 6 to 8 included the inert solvent and an I:Co ratio within the critical range but the temperature was outside applicant's range; as a consequence ethanol selectivity was negligible at only a few percent even through the methanol conversion was high. This deomonstrates that the reaction temperature must be within the range found critical in order to obtain high ethanol selectivity at high methanol conversion.

Runs 9 and 10 included the inert solvent but the I:Co ratio was higher than the critical upper limit and the reaction temperature was below the critical lower limit. The selectivity to ethanol was negligible though the methanol conversion was acceptable.

The results of the comparative data in Table III and Table IV establish the critical relationship of the three parameters found necessary by applicant, namely, the need for an inert solvent, an I:Co mole ratio of from 0.1:1 to 4:1 and a temperature of from greater than 180° C. to about 220° C. Under these limited and critical conditions one achieves both high methanol conversion and high selectivity to the formation of ethanol during the homologation reaction of methanol with hydrogen and carbon monoxide. The data clearly establishes that deviation from these conditions precludes one from obtaining both.

The presence of inert solvent by itself does not lead to high selectivity at high methanol conversion. Neither does the critical reaction temperature, by itself, nor does the critical I:Co mole ratio by itself. Furthermore no two of these critical parameters without the third will give high ethanol selectivity at high methanol conversion. Thus, if one runs at proper temperature and I:Co ratio but with no solent, poor selectivity is the result; if one runs with solvent at proper temperature but at an I:Co ratio outside the critical limits poor conversion is observed at I:Co ratios below that found critical and poor selectivity is observed at I:Co ratios above that found critical; if one runs with solvent and proper I:Co mole ratio but a temperature outside the critical limits, poor selectivity results. No one critical parameter is controlling nor do any two in combination give good results. Only when all three critical parameters are present within the defined limits and acting in concert is the high ethanol selectivity at high methanol conversion attained. It is completely unobvious why this should be so. There is an unobvious synergistic effect when all three critical parameters are employed. When any one of these parameters is missing the results obtained are poor. The beneficial synergistic effect obtained when all three critical parameters are present is entirely unobvious and could not have been predicted from the known prior art.

What is claimed is:

1. In a process for selectively producing ethanol from the reaction of methanol, hydrogen and carbon monoxide at a pressure of from 1,000 psig to 10,000 psig and a $H_2:CO$ mole ratio of from 1:10 to 10:1 and wherein the reaction is catalyzed by a catalyst system consisting essentially of cobalt and iodide ion, the improvement consisting of carrying out the reaction at a temperature of from greater than 180° C. to 220° C. in the presence of a substantially inert solvent from the group consisting of dioxane, toluene, tetrahydrofurane, the dimethyl ether of tetraethylene glycol and 1,2-dimethoxybenzene at an iodide to cobalt mole ratio of 0.1:1 to 4:1 and wherein the volume ratio concentration of said inert solvent to methanol is from 0.5:1 to 100:1.

2. The improved process as claimed in claim 1 wherein said temperature is from 190° C. to 210° C.

3. The improved process as claimed in claim 1 wherein said inert solvent is present in a volume ratio of from 0.5:1 to 100:1 based on the volume of methanol present.

4. The improved process as claimed in claim 1 wherein said inert solvent is present in a volume ratio of from 1:1 to 10:1 based on the volume of methanol present.

5. The improved process as claimed in claim 3 wherein the volume ratio is from 1:1 to 3:1.

6. The improved process as claimed in claim 1 wherein said substantially inert solvent is dioxane.

7. The improved process as claimed in claim 1 wherein the mole ratio of iodide to cobalt is from 0.5:1 to 2:1.

8. The improved process as claimed in claim 1 wherein the cobalt-iodide catalyst system is present at from 0.5 weight percent to 25 weight percent, based on the amount of methanol present.

9. The improved process as claimed in claim 1 wherein the cobalt-iodide catalyst system is present at from 1 weight percent to 10 weight percent, based on the amount of methanol present.

10. The improved process as claimed in claim 1 wherein the source of cobalt is cobalt acetate.

11. The improved process as claimed in claim 1 wherein the source of iodide is elemental iodine.

* * * * *